United States Patent
Baltruschat (12)

(10) Patent No.: US 6,224,745 B1
(45) Date of Patent: *May 1, 2001

(54) PROCESS AND DEVICE FOR CONTINUOUSLY DETECTING AT LEAST ONE SUBSTANCE IN A GASEOUS OR LIQUID MIXTURE BY MEANS OF A SENSOR ELECTRODE

(75) Inventor: Helmut Baltruschat, Luigi-Pirandello (DE)

(73) Assignee: Private Universitat, Witten (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,452
(22) PCT Filed: Apr. 26, 1996
(86) PCT No.: PCT/EP96/01752
 § 371 Date: Mar. 5, 1998
 § 102(e) Date: Mar. 5, 1998
(87) PCT Pub. No.: WO96/34275
 PCT Pub. Date: Oct. 31, 1996

(30) Foreign Application Priority Data

Apr. 27, 1995 (DE) .............................. 195 15 524

(51) Int. Cl.[7] ............................................. G01F 1/64
(52) U.S. Cl. ................................... 205/775; 205/780
(58) Field of Search ..................... 205/775, 778.5, 205/779.5, 780, 787; 204/400, 431

(56) References Cited

U.S. PATENT DOCUMENTS 4,072,576 * 2/1978 Arwin et al. ............................ 435/4
4,812,210 * 3/1989 Bonivert et al. ...................... 205/787
4,919,770 4/1990 Preidel et al. ..................... 204/153.1

(List continued on next page.)

FOREIGN PATENT DOCUMENTS

| 32 28 542 A1 | 2/1984 | (DE) . |
| 36 27 799 C2 | 2/1988 | (DE) . |
| 2 351 412 | 12/1977 | (FR) . |
| 2280034 | 1/1995 | (GB) . |
| WO 91 17433 | 11/1991 | (WO) . |
| WO 94 15210 | 7/1994 | (WO) . |

OTHER PUBLICATIONS

"Zykllschas Potential Rungverfahren mlt Gberlagerter Wechselspannung Zur Glucosebesltmmung im Blut", Preidel et al., Dechema–Monographien Band 117–VCH Verlagsgesellschaft 1989, pp. 59–72 (English abstract on p. 60).
"Selectivity Enhancement of Amperometric Gas Detection Cells: Linear Potential Sweep Voltammetry (LPSV) After Specific Adsorption at Fixed Potentials", Ege et al., Sensors and Actuators, B 4, 1991, pp. 519–524.

(List continued on next page.)

Primary Examiner—Robert J. Warden, Sr.
Assistant Examiner—Andrew Aldag
(74) Attorney, Agent, or Firm—Marshall, O'Toole, Gerstein, Murray & Borun

(57) ABSTRACT

Processes and devices are disclosed for continuously detecting at least one substance in a gaseous or liquid mixture by means of a sensor electrode to which is applied a variable potential. In an alternative, the substances are concentrated at the surface of the sensor electrode, their concentration is determined by measuring the electrode capacity, the thus obtained measurement value is correlated with the substance and the substance. concentrated at the surface of the sensor electrode is then removed. In another alternative, one or several detection cycles are carried out. In each detection cycle, at least one substance is concentrated at the surface of the sensor electrode, the potential is brought to at least one potential characteristic of the electrochemical reaction of at least one substance, the resulting current is measured and the thus obtained measurement values are correlated with the substances.

10 Claims, 6 Drawing Sheets

U.S. PATENT DOCUMENTS 5,683,569 * 11/1997 Chung et al. .................. 205/775
5,725,754 * 3/1998 Belford .......................... 205/789
5,770,038 * 6/1998 Iwama et al. .................. 205/775
5,846,744 * 12/1998 Athey et al. .................. 435/7.9

OTHER PUBLICATIONS

"On the Quantitative Determination of Carbon Dioxide in Air. A New Sensor Technique Using Anodic Adsorbate Stripping", Küver et al., J. Electroanal. Chem., 353, 1993, pp. 255–263.

"Polarographische und Voltammetrische Methoden", Nürnberg et al., Methodicum Chimicum, vol. 1/1, Stuttgart, pp. 606–630, 1973.

"An Impedance Based Ultra–Thin Platinum Island Film Glucose Sensor", Kasapbasioglu et al., Sensors and Actuators B, 13–14, pp. 749–751, 1993.

* cited by examiner

PROCESS AND DEVICE FOR CONTINUOUSLY DETECTING AT LEAST ONE SUBSTANCE IN A GASEOUS OR LIQUID MIXTURE BY MEANS OF A SENSOR ELECTRODE

FIELD OF THE INVENTION

The invention is concerned with a method and with a device for continuously detecting at least one substance in the gaseous or liquid mixture by means of a sensor electrode to which a variable potential is applied.

BACKGROUND OF THE INVENTION

The demand for a problem-free, rapid and cost-effective detection method for substances, especially for harmful substances, has increased recently, one of the reasons being the increased demands for environmental protection. In order to comply with harmful-substance limiting values (for example, in controlling and reducing emissions) it is necessary to be able to detect harmful substance concentrations in gaseous or liquid media reliably and continuously, possibly by the use of electrochemical sensors. In process monitoring, too, the control of the concentration of products, starting materials and impurities may be necessary for optimum performance of the process. However, rapid detection is made difficult by the fact that the materials or substances are frequently slow to react.

Frequently, electrochemical detection is based on the amperometric principle and is aimed at the quantitative detection of a material component.

For this purpose, substances ($Cl_2$, HCl, $SO_2$, $NO_x$, $H_2CO$, etc.) are reacted electrochemically, that is, by an oxidation or reduction reaction on a sensor electrode to which a constant potential is applied.

The current flowing can be set in relation to the concentration of the substance to be detected. The selectivity of a sensor electrode based on this working principle is limited by the electrode material used and by the potential that can be applied to the electrode. The potential that can be applied is limited to a range of values at which the oxygen of the air is not reduced and/or the electrolyte for the substance to be detected is not decomposed. Namely, the currents produced by these perturbing effects would overlap the actual measured signal almost completely. Moreover, some substances are not sufficiently reacted in the available potential range or poison the sensor electrode by adsorption, so that they cannot be detected by this method. These substances include many unsaturated compounds, halogenated hydrocarbons and aromatics.

Qualitative and quantitative electrochemical detection can be achieved by voltametric techniques. Here, the substance to be detected is not reacted at the electrode at a fixed potential. Rather, oxidation or reduction of the substance is catalyzed successively while a continuously varying potential is applied. The recorded relationship between the amount of charge passing through or current and applied potential can be correlated with the quantity and also with the nature of the substance to be detected.

In another electrochemical detection method, called the alternating current method, an alternating voltage is superimposed on the voltage applied to an electrode. The alternating current flowing through is measured. The measured alternating current is shifted in phase with respect to the applied alternating potential, namely, because of the electrode capacitance, which is changed by the adsorption of the substance to be detected and also because of oxidation and reduction processes. Therefore, a complex resistance is defined, which is called impedance below, which describes the processes on the electrode surface appropriately. Its frequency-dependent and potential-dependent real and imaginary parts give information about the concentration of the substance to be detected.

A detection method, which is similar to the alternating-current method is tensametry, known from the analysis for solutions (see for example Nürnberg et al., in Methodicum Chimicum, Volume 1/1, Stuttgart 1973). However, in such methods, the sample with the substance to be detected must always "be prepared" manually to some extent, that is, interfering impurities must be removed and the oxygen of the air must be excluded.

Thus, continuous detection cannot be performed with these two known methods—alternating-current method and tensametry.

In this connection, the determination of concentration of blood glucose is also known (Kasapbasioglu et. al., Sensors and Actuators B, 13–14 (1993), p. 749). Here, glucose is oxidized directly electrochemically to gluconic acid on a membrane-covered electrode made of a noble metal. The electrode functions as an electrocatalyst, to which a potential program that decreases and increases stepwise is applied. At each step, an alternating potential with a high frequency and one with a low frequency are superimposed onto the potential. The glucose concentration in the blood is determined from the resulting real and imaginary part of the impedance at certain potential steps.

Furthermore, it is known that the selectivity and sensitivity of an electrode can be increased in an electrochemical detection method by utilizing the adsorption or absorption of the substance to be detected on the electrode surface. The adsorption or absorption can be supported, weakened or eliminated by the applied potential or potential program. The substance to be detected is adsorbed at a potential at which the substance is not electro-chemically active. The amount adsorbed as a function of time is then correlated with the concentration of the substance to be detected.

A method is known from the technical journal "Sensors and Actuators B", Ege et al., 4 (1991), p. 519, with which the reactive carbon monoxide CO in a $CO/H_2$ mixture can be detected quantitatively based on the amperometric principle. For the detection, first the carbon monoxide component is adsorbed on a platinum electrode and then reacted electrochemically. The carbon monoxide is adsorbed specifically at a potential at which it is not electrochemically active or is not reacted. After adsorption of the carbon monoxide to the saturation value, the potential is increased to a value at which the carbon monoxide is oxidized. The amount of charge flowing during oxidation is measured and is integrated over the oxidation time. The measured signal thus obtained is correlated with the concentration of the carbon monoxide. However, the amount of charge flowing is additionally superimposed by amounts of charge stemming from the electrochemical reaction of additionally adsorbed substances, such as oxygen. This additional amount of flowing current is determined in another reference cycle, in order to correct the measured signal. In this reference cycle, a potential is applied over a very short period of time to adsorb the additionally adsorbed substances. The time period is made so short that the carbon monoxide is not adsorbed on the electrode surface of the sensor. Then the potential is brought to a suitable value for the electrochemical reaction of these additionally adsorbed substances. The amount of charge flowing during this electrochemical reaction is used as correction value, because it is influenced only by the additionally adsorbed substances. Minimum CO concentrations up to 0.05% CO can be detected in a $CO/H_2$ mixture. However, this known method cannot provide continuous detection either. Moreover, there is no suitable sensor for the commercial utilization of this method of detection.

Similarly, the reactive carbon dioxide, $CO_2$, can be detected quantitatively in air at concentrations from 5% to 0.3% $CO_2$ (Küver et al.; J. Electroanal. Chem., 353 (1993), p. 255).

It is also known that several substances can be detected quantitatively simultaneously with the aid of a chain of electrodes which mostly consist of different electrode materials. Different potentials are applied to the individual electrodes and one substance reacts electrochemically at each of these potentials. The measured signals obtained at the individual electrodes are correlated with the individual substance concentrations using pattern recognition technology.

The electrochemical detection methods mentioned above are not suitable for rapid, continuous, both qualitative as well as quantitative detection, or are very expensive. Moreover, substances with low reactivity cannot be detected with these known detection methods or can only be detected at high concentrations.

In general, known electrochemical detection methods are characterized by the fact that the selectivity is frequently too low. Similarly, most of the sensors based on these detection methods do not satisfy the general criteria of a sensor: The detection should occur rapidly and continuously without preparation of the sample "on location" with a time constant of the order of one or at most a few minutes. In addition, the sensor should operate in the ambient atmosphere, that is, generally in the presence of the oxygen of air and should also be cost-effective.

The goal of the invention is to provide further methods and devices for continuous and quantitative as well as qualitative detection of substances in gaseous or liquid mixtures.

SUMMARY OF THE DISCLOSURE

In accordance with another aspect of the invention, a method is provided for the continuous detection of a substance in a gaseous or liquid mixture, with the aid of a sensor electrode to which a variable potential is applied, in which method the substance is enriched at the surface of the sensor electrode, the enrichment is determined with the aid of measurement of the electrode capacitance of the sensor electrode, the measured value thus obtained is correlated with the substance and then the substance enriched on the surface of the sensor electrode is removed. In accordance with another aspect of the invention, a device suitable for carrying out the above-described method is provided with means for carrying out the individual process steps listed above.

The detection method described above is designated below as a modified alternating-current method. Here, the applied potential is preferably chosen in such a way that the substance is enriched on the electrode surface of the sensor without an electrochemical reaction. The ions of the electrolyte form a double layer at the sensor electrode. Together with the electrode surface of the sensor, this double layer acts as a type of plate capacitor. The degree of enrichment of the substance changes the capacitance of this plate capacitor or sensor electrode by the adsorbate blocking a part of the electrode surface. The capacitance of the sensor electrode can be followed with the aid of a suitable electronic measurement method and correlated with the concentration of the substance. This modified alternating current method is characterized by high sensitivity to changes in the structure of the double layer. Thus, it is especially suitable for simple qualitative and quantitative detection of small concentrations of surface-active substances, especially halogenated hydrocarbons and highly volatile organic solvents.

First of all, it could be shown that the substance to be detected is adsorbed in spite of simultaneous reduction of the oxygen of the air (even when the concentration of the oxygen of the air is greater by a factor of $10^5$ to $10^6$ or even more than the concentration of the substance to be detected) and, thus, the electrode capacitance—and hence also the concentration of the substance to be detected—can be detected with the reduction of oxygen occurring simultaneously.

The enrichment of one or several substances present in a mixture can be influenced among others by the adsorption time and the applied adsorption potential. The adsorption time of a substance depends on different thermodynamic and kinetic properties of the various substances in the mixture. By suitable selection of the applied adsorption potential and other parameters (see below), the substance can be detected selectively in the mixture.

With the modified detection method, the disadvantages of the known detection methods described above are avoided. The method is universally applicable, especially to substances with low reactivity.

In a preferred embodiment, the electrode capacitance of the sensor electrode is determined by an impedance measurement. Preferably, a dc voltage with a superimposed low-frequency alternating voltage is applied to the sensor electrode for this purpose. The impedance of the sensor electrode or of the double layer is then determined based on the phase shift and the change of amplitude of the alternating current flowing as a result of the applied low-frequency alternating voltage.

Preferably, the frequency of the low-frequency alternating voltage is optimized with reference to the impedance measurements.

In a preferred detection method, the concentration of the substance is determined based on the difference of the electrode capacitance of the sensor electrodes, with and without enrichment of the substance on the electrode surface. Here, preferably in a first step, a dc voltage with a superimposed alternating voltage is applied to the sensor electrode as potential. The potential is chosen so that the substance is reacted electrochemically and therefore is not enriched. Thus, in this first step, the electrode surface is activated. Then the electrode capacitance is measured with the electrode surface being activated or free. In a second step, the potential is preferably brought to a value at which the substance to be detected is enriched at the electrode surface of the sensor and remains there essentially unreacted. Then the electrode capacitance is measured with the electrode surface being occupied. The concentration value of the substance to be detected is calculated from the difference of the electrode capacitances measured in the two steps.

In an especially preferred detection method, the concentration of the substance is determined based on the change of the capacitance of the sensor electrode as a function of time. The change of the electrode capacitance as a function of time can be measured quasi-differentially—at successive points in time during the enrichment process—or as an average—measuring it at the beginning and at the end of the enrichment phase. It is proportional to the time change of the imaginary part of the alternating current caused by the applied low-frequency alternating voltage. This flowing alternating current can be measured by a simple technology. Thus, the time change of the electrode capacitance and the concomitant enrichment of the substance at the electrode surface can be followed advantageously almost continuously. This time change is then correlated with the substance concentration using known relationships, for example, calibration, which is carried out once during manufacture or at large time intervals.

The parameters measured in this detection method—for example, enrichment time, enrichment potential and frequency of the applied alternating voltage—provide sufficient possible combinations for accurate, simple, qualitative and quantitative detection of substances in a gaseous or liquid mixture, especially at low concentrations.

Preferably, in order to remove the substance enriched at the electrode surface, the potential is brought to a potential characteristic for its electrochemical reaction and/or desorption. For the purpose of continuous detection, it is necessary that the electrode surface of the sensor used be freed completely of the enriched substance from time to time. This can be done with the aid of the so-called oxidation cycles. Here, the electrode surface is cleaned and activated by appropriate selection of the applied potential by first electrochemically reacting and/or desorbing the enriched substance or by displacing it with adsorbed oxygen. Finally, the reacted substance or the adsorbed oxygen is desorbed completely, for example, by reducing the potential or by other methods.

Furthermore, the enrichment is preferably ended when the measured electrode capacitance or the time change of the electrode capacitance of the sensor electrode reaches a predetermined value. Hereby, advantageously, the occupation of the electrode surface with the substance to be enriched is followed. Using a predetermined value, the relationship of the response time to the sensitivity of the sensor can be varied. The response time depends automatically on the time during which the substance to be detected is enriched on the electrode surface to an amount which is sufficient for the measured signal to be evaluated. With the predetermined value, thus the sensor performs the detection at maximum sensor sensitivity and minimum response time. The reactivity and sensitivity of the sensor can thus be optimized advantageously and especially simply.

Preferably, the measured value thus obtained is optionally normalized using a measured value obtained through at least one other measurement of the electrode capacitance of the sensor electrode, in which step essentially not the substance to be detected, but only oxygen or hydrogen is enriched at the sensor electrode. Thus, for this normalization, the additional measured value can be a measured value that is obtained either in a separate measurement or—when measuring the time change of the electrode capacitance as an average—it can be the value measured at the beginning of the enrichment phase. With this normalization, the alterations, aging or wear phenomena of the electrode surface are advantageously taken into consideration and the measured signal is appropriately corrected. The normalization is based on the fact that adsorption of pure oxygen or hydrogen on the sensor electrode is influenced adversely by the quality of the sensor electrode surface to the same extent as the enrichment of the substance to be detected. Preferably, the measured value can also be normalized with the aid of the electrode capacitance.

According to another aspect of the invention, a method is provided for the continuous detection of a substance in a liquid mixture with the aid of a sensor electrode to which a variable potential is applied, by enriching the substance on the surface of the sensor electrode, then bringing the potential to a potential value which is characteristic for the electrochemical reaction of the substance, measuring the current thus produced and correlating the obtained measured value with the substance. In accordance with another aspect of the invention, a device is provided for carrying out the method described above, with means which carry out the individual process steps listed above.

The detection method described in the preceding paragraph will be called below the liquid-phase potential method. With this liquid phase potential method at least one substance is detected in a liquid phase. Similarly to the modified alternating-current method, it also uses the enrichment of the substance to be detected on an electrode surface to which an appropriate potential is applied. After enrichment, preferably, the enriched substance is oxidized or reduced at a potential characteristic for the electrochemical reaction. The current resulting from the electrochemical reaction is then correlated with the enriched substance and finally with the substance concentration in the liquid phase or solution to be investigated. With the aid of the enrichment, the local substance concentration near the sensor electrode is highly increased, so that the current flowing during the subsequent electrochemical reaction provides a larger measured signal. A sensor to be used in this liquid-phase potential method thus advantageously also detects substances with low reactivity, because this sensor is overall more sensitive than the known sensors. Furthermore, this sensor can be optimized through the parameters of enrichment potential and enrichment time.

According to still another aspect of the invention, a method is provided for the continuous detection of at least two substances in a gaseous or liquid mixture with the aid of a sensor electrode to which a variable potential is applied, in which method at least two detection cycles are performed and at least one substance is enriched at the surface of the sensor electrode per detection cycle, after which the potential is brought to a potential characteristic for the electrochemical reaction of at least one substance and the current produced thereby is measured, and, subsequently, the measured values thus obtained are correlated with the substance. In accordance with another aspect of the invention, a device is provided for carrying out the method described above, with means which carry out the individual process steps listed above.

The detection method described in the preceding paragraph will be referred to below as the general potential method. It serves for the detection of at least two substances in a gaseous or liquid mixture. For this purpose, the potential applied to the sensor electrode goes through a given potential program in each detection cycle.

The potential program can be the following: first a potential is applied at which at least one of the substances is enriched at the electrode surface, whereby the time available for the enrichment is preferably variable. Then the potential is changed to a value at which at least one of the substances enriched on the sensor electrode is reacted electrochemically. The current flowing during this process is measured. The potential is changed, preferably by a jump, to a value at which again at least one substance is enriched at the electrode surface of the sensor. For the detection of several substances in a mixture, in this special potential program, as many enrichment steps must be carried out as many different substances are to be detected. At least one substance is reacted electrochemically in each of these enrichment steps.

For example, in the detection of two substances in a two-substance mixture, in the second enrichment step, additionally, the substance which is not enriched in the first enrichment step is additionally enriched. When both substances were enriched in the first enrichment step at the electrode surface, then, in the second enrichment step, a potential is applied at which only one of the two substances is enriched. After the particular enrichment steps, a potential is applied at which the enriched substance or substances are reacted electrochemically. The current flowing during this time is determined.

In case of three substances to be determined, for example, the potential program can be the following: when, in a first enrichment step, substances 1, 2 and 3 are enriched, and in a second step substances 1 and 2 are enriched, then, in this special potential program, in a third step either only substance 1 or substance 2 may be enriched. Enrichment of substance 3 does not lead to an appropriate independent detection of all three substances.

However, alternatively, the potential program can also be the following: first a potential is applied at which only one or several substances is/are enriched. Then, the individual substances are reacted or oxidized at characteristic potentials (when more than two substances to be detected are present, several enrichment steps can also be performed; however, for this purpose, the number of enrichment steps does not have to be as many as the number of substances to be detected contained in the sample).

The currents flowing at the different electrochemical reactions are used to determine the concentrations of the particular substances.

With this potential program, the cross-sensitivity of a sensor can be advantageously highly minimized. In addition, the detection of several substances can be done in the presence of the others advantageously, using only one sensor cell, instead of one sensor cell for each substance to be detected, as done in the prior art. The enrichment with continuous detection also provides the advantage that the sensor selectivity can be optimized via the enrichment potential and the enrichment time.

With these two potential methods according to the invention (liquid phase and general), the disadvantages of the known detection methods of the prior art can be avoided. They are universally applicable, especially to substances with low reactivity.

The variable potential can be altered cyclically in all three detection methods according to the invention. After completion of a potential program with enrichments and subsequent electrochemical reactions, the potential is brought again to the initial value of the same potential program and is thus available for the next detection cycle. Accordingly, in this way, the concentration of at least one substance to be detected can be followed quasi-continuously.

In order to maintain the sensitivity of the sensor electrode through a continuous detection operation, the electrode surface must be freed, in an appropriate desorption step, both from the oxidized and reduced enriched layer of the substance to be detected as well as from the additionally adsorbed oxygen layer (or also hydrogen layer). For this purpose, in a first step, preferably the enrichment layer is oxidized and an oxygen layer is enriched. In the next desorption step, preferably, a low potential is applied to the sensor electrode for a short time during which the enriched oxygen layer is reduced (optionally, the entire enrichment layer is desorbed). Then the potential is again brought to the potential that is characteristic for the electrochemical reaction. Repeated passage through these desorption steps ensures that the electrode surface is actually unoccupied. Additionally, the sensor electrode can be activated by adsorbing oxygen in a first step and desorbing it again in a second step.

In another practical example of a continuous detection method, the potential which is characteristic for the electrochemical reaction is changed linearly in time. For this purpose, after the enrichment step, the potential is brought to a potential value, preferably in a jump, and then varied linearly as a function of time. Thus, the potential goes through a range at a given potential change rate. Due to the sudden change of the potential values, one obtains an enrichment step which is accurately defined in time and also the time for this enrichment step and thus for the entire detection cycle is shortened. This value of the potential change rate has an upper limit by the fact that the electrochemically reacted substances should find sufficient time to desorb. The potential change rate should not be chosen too slow, because otherwise the response time of the sensor would be increased. Owing to the linear increase of the potential from an initial value to an end value, all substances that are reacted between these two electrochemical values are advantageously desorbed from the electrode surface.

Furthermore, the concentration of the substance is determined preferably through the current produced by the electrochemical reaction at a specific potential. Preferably, for this purpose, the maximum current flowing during the electrochemical reaction is determined instead of the current integrated in time over the entire electrochemical reaction and is thus correlated with the enriched substance concentration. The measured current can be correlated with the substance concentration using a previously performed calibration.

Preferably, the measured value(s) obtained with the above detection method is/are correlated with a measured value, called oxygen value below, in which the oxygen value is obtained through at least one other detection cycle—called reference cycle below—in which the substance is not enriched in a first step on the sensor electrode. If said potential values are in ranges in which other substances which perturb the detection are reacted electrochemically or enriched simultaneously, then the additionally flowing currents must be taken into consideration in reference cycles in the determination of the substance concentrations. These interfering substances are present in the electrolyte initially, such as bound oxygen or water. During the reference cycle, no substance is enriched, for example, only oxygen is adsorbed. Then the oxygen is oxidized or reduced at the same potential at which the substance to be detected was already reacted electrochemically and the current flowing during this process is determined. For the purpose of measurement value correction, the current measured in the reference cycle is subtracted from the current measured in a normal detection cycle.

In this method, the measured value thus obtained is preferably normalized to the oxygen value determined in the reference cycle. With this normalization, changes, alterations or wear phenomena of the electrode surface are taken into consideration advantageously and the measured signal corrected correspondingly. The normalization is based on the fact that pure oxygen or hydrogen adsorption is influenced adversely to the same extent by the quality of the sensor electrode surface as the enrichment of the substance to be enriched on the sensor electrode. Preferably, the measured values are also normalized with the aid of the electrode capacitance.

Especially preferably, during the potential method according to the invention (liquid phase and general), the electrode capacitance is measured and the enrichment ended when the electrode capacitance or the time change of the electrode capacitance reaches a predetermined value. In this detection method—called combined detection method below—in principle, the potential method (liquid phase and general) according to the invention, is combined with the modified alternating current method according to the invention. The enrichment is followed as in the modified alternating current method. The electrochemical reaction is started only when a sufficient amount of substance has become enriched on the electrode surface. The resulting oxidation current thus yields a sufficiently large measurement signal and thus concomitantly a reliable concentration result for the substance to be detected. Preferably the concentrations of the individual substances to be detected are determined only through the enrichment, and the determination of the other substances is carried out either in combination, through a previous enrichment and subsequent electrochemical reaction, or directly through an electrochemical reaction.

In another preferred variation of the modified alternating current method or potential method (liquid phase, general or combined), the substance to be detected is first reacted electrochemically at the sensor electrode or at another electrode at an applied potential and at least one product thus obtained is then detected by the sensor electrode. If a substance to be detected is characterized by a small tendency to become enriched at the sensor electrode used, then this substance can advantageously be reacted electrochemically at an electrode at a given potential to form an intermediate product. The intermediate product formed should then be able to be enriched at the electrode surface of the sensor electrode at another potential value. The final detection of this intermediate product is then carried out either through the modified alternating current method presented above or by one of the potential methods. Preferably, the electrode necessary for the production of the intermediate product can be separated in space from the sensor electrode, so that the substance that has a low tendency to become enriched can be detected continuously. The spatial separation must not be too large, so that the intermediate product can diffuse from the separate electrode to the sensor electrode within a short time—preferably in fractions of a minute.

Preferably, the detection can be optimized through the parameters of electrode material, electrolyte composition, enrichment, enrichment potential, potential for electrochemical reaction and/or time change of the potential for the electrochemical reaction. The detection methods according to the invention provide a multiplicity of optimization parameters for a highly sensitive and selective sensor electrode. The optimization parameters for the enrichment—enrichment time, enrichment potential, electrode material and electrolyte composition—as well as for the electrochemical reaction—electrolyte composition, electrode material, characteristic potential and its time change—can vary.

In the devices according to the invention, the sensor electrode is preferably a membrane provided with an electrocatalyst on one side. The sensor electrode is wetted mostly on one side with the electrolyte solution necessary for the electrochemical detection. The electrolyte solution is preferably hygroscopic, so that evaporation of the water is largely avoided and that its composition—concentration of the conducting salt—remains as constant as possible. Preferably, the membrane is made of teflon and/or the electrocatalyst is a thin platinum, rhodium or palladium layer applied by sputtering. Platinum is characterized by good enrichment properties toward a number of substances, while palladium is especially suitable for the detection of saturated halogenated hydrocarbons. However, other metals of the platinum group can also be used as electrocatalyst.

The test liquid itself can replace the electrolyte solution for the liquid detection method. Here, the membrane is preferably prepared from a porous, hydrophilic or ion-conducting material (for example, Nafion), and the electrocatalyst is applied onto the side that faces the test liquid—and not the electrolyte liquid. For this purpose, the electrocatalyst is applied in such a thin layer that the membrane with the electrocatalyst is still porous or ion-conducting. Furthermore, the sample liquid side of the membrane can be provided with a thin Nafion or cellulose acetate film, as protecting film. With this structure, the sensor electrode can be used relatively universally in various (even nonaqueous or poorly conducting) liquids.

For the gaseous detection method, the electrocatalyst is sputtered onto the side of the membrane which faces the electrolyte solution. Here, the gaseous substances to be detected can diffuse through the membrane and the electrocatalyst and dissolve in the electrolyte solution before they reach the electrode surface. However, for the gaseous detection method, the sensor electrode described above for the liquid detection method may also be used.

The invention complex will be explained in more detail below with the aid of practical examples and the drawings.

DETAILED DESCRIPTION OF THE PREFERRED EMBODIMENTS

Figure 1:
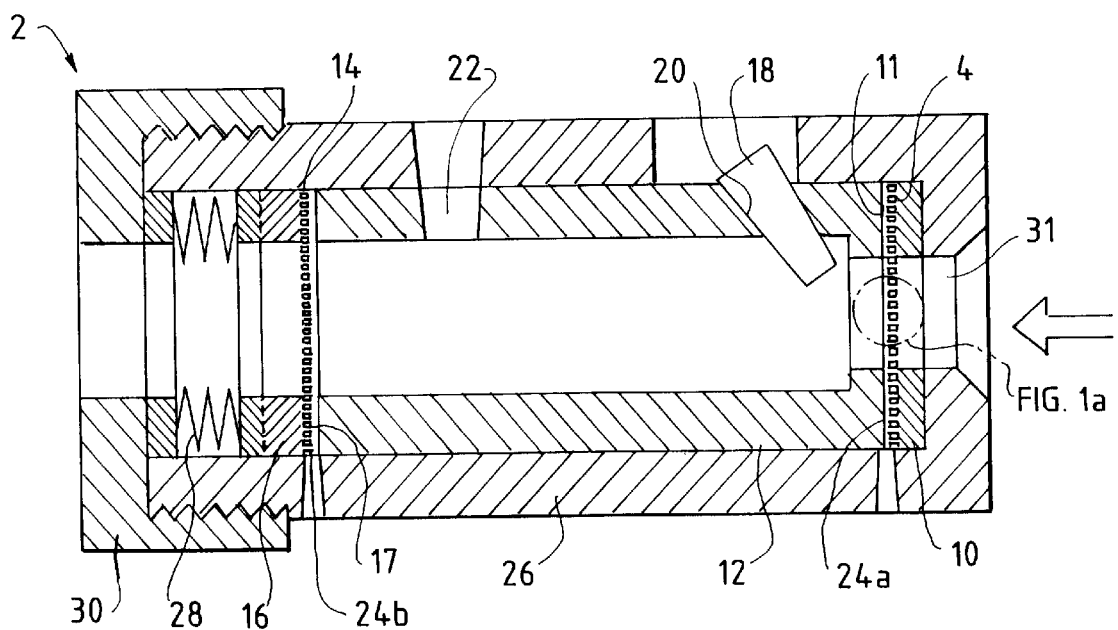
FIG. 1 illustrates, in a schematic representation, a cross-section through a sensor, where the sensor electrode is also shown in detail as a model.
Figure 1A:
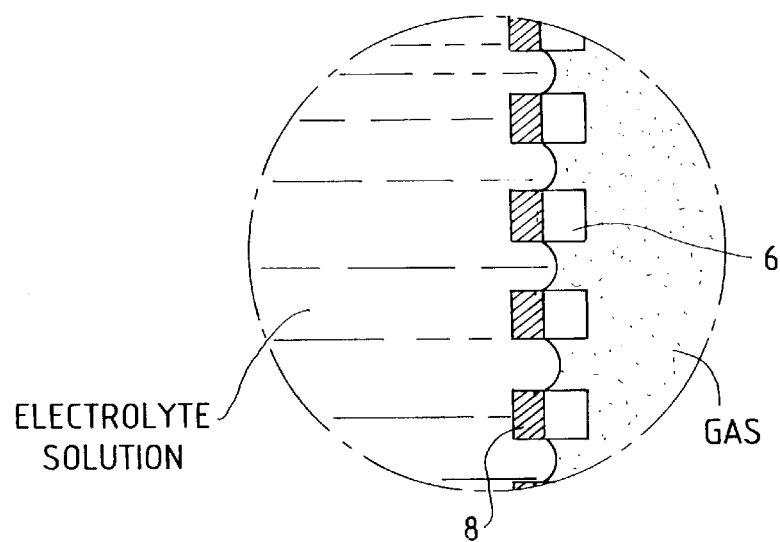

FIG. 1 shows in a schematic representation a cross-section through a sensor generally designated 2, which is suitable for carrying out the represented detection method of substances in gaseous mixtures.

The core part of sensor 2 is a sensor electrode 4 consisting of a teflon membrane 6, shown schematically in detail in an enlarged form. The teflon membrane 6 preferably has a thickness of 75 μm, a pore size of 0.2 μm and a diameter of 6 mm. It separates the gaseous mixture with the substance to be detected from an electrolyte solution necessary for the electrochemical detection. The electrolyte solution is selected to be strongly hygroscopic (for example, perchloric or sulfuric acid) and thus prevents rapid drying of sensor 2, so that the electrolyte concentration in the inner space of sensor 2 hardly changes at all. The teflon membrane 6 is sputtered with an electrocatalyst 8 (for example, platinum) on the side facing the electrolyte solution. A thin, noble metal layer with a layer thickness of preferably 90 nm is produced. In addition, the roughness factor of the noble metal layer is reduced considerably in comparison to the roughness factor of known sensor electrodes for amperometric detection methods. The teflon membrane 6 thus modified functions at the same time as a sensor and as a gas-diffusion electrode. It is secured tightly to a sensor housing 12, with the aid of a pressing disk 10 through an O-ring 11. The sensor electrode 4 is dimensioned in such a way that, on the one hand, edge effects (interfering electrochemical processes at the edge or in the electrolyte gaps at the seal) become negligible, while, on the other hand, the resistance of the metal layer toward the center of the sensor electrode becomes sufficiently small. The resistance is measured here from the edge of the sensor electrode 4 where the electrical contact to an external electronic is provided, to the center of the sensor electrode 4, where the electrochemical processes occur mainly—such as enrichment and electrochemical reaction, etc.

The sensor electrode 4 is embedded into the cylindrical sensor housing 12 in such a way that it and an opposite counter-electrode 14, as components of a three-electrode arrangement, close this inner sensor housing 12 tightly at the open sides. The counter-electrode 14 is pressed tightly against sensor housing 12 with the aid of a ring 16, a means to secure against turning and an O-ring 17. Preferably, a reference electrode 18, for example, a hydrogen electrode, is introduced through a conical bore 20 into the cylinder wall of sensor housing 12, so that it can be placed in the immediate vicinity of the sensor electrode 4. The sensor 2 can be filled with electrolyte solution through another conical bore 22. This bore 22 is then closed for the practical operation of sensor 2, in order to prevent running out of the electrolyte solution. Optionally, the gaseous products that are formed in the electrolyte solution or the gases that are formed at the counter-electrode 14 can be liberated directly through the porous teflon membrane 6, as long as their amount, based on the area of the teflon membrane 6, is not too large. Therefore, the area of the teflon membrane 6 must be greater than the area of the sensor electrode 4 or of the electrocatalyst. Thin wires 24a and 24b provide the electrical contact of sensor electrode 4 and counter-electrode 14 toward the outside.

In order to provide good tightness or a high pressing pressure of sensor 2, the sensor housing 12 is surrounded by a steel mantle 26, which presses the sensor housing 12 together under pressure, with the aid of leaf springs 28 and a lock nut 30.

The gaseous mixture with the substance(s) to be detected enters through an opening 31 of the steel mantle 26 and the pressing disk 10 in the direction shown by the arrow and impinges onto the outside of the porous teflon membrane 6. From there, it goes through the pores of the teflon membrane 6 inside sensor housing 12 and dissolves in the electrolyte solution located there.

The sensor 2, together with the corresponding electronics for carrying out the individual detection methods according to the invention (potential program, automatic ending of the enrichment phase, etc.), can be dimensioned in such a way that it is easily transportable. For this purpose, the heavy steel mantle 26 can be replaced by another suitable housing.

Overall, the sensor 2 has good contact between the thin wires 24a and 24b and the respective electrocatalyst layer of sensor electrode 4 or counter-electrode 14, especially with regard to a small distance of the reference electrode from the working electrode, has small dimensions; a special type of the sensor electrode 4 as well as a small roughness factor of the electro-catalyst layer were optimized for the detection method of the invention.

Figure 2:
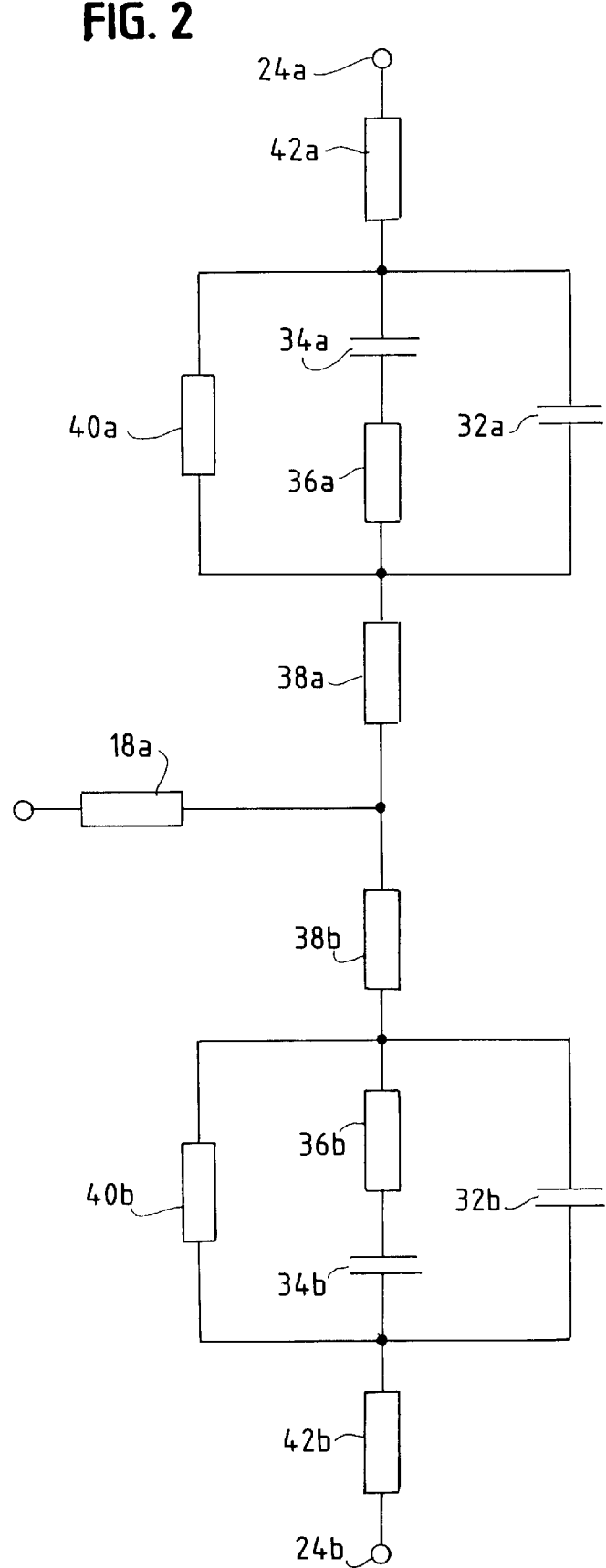
FIG. 2 illustrates, an equivalent circuit for the behavior of the sensor electrode with enriched substance in the modified alternating current method.

FIG. 2 shows an equivalent circuit for the electrical behavior of sensor electrode 4, counter-electrode 14 and reference electrode 18 in the modified alternating current method.

Ions and solvent molecules with dipole character (that is, water molecules) interact with the metallic electrode surface 8 of sensor electrode 4 and of counter-electrode 14 and develop an electrolytic double layer there. In the simplest case, this electrolytic double layer behaves as a plate capacitor 32a or 32b with a certain double-layer capacitance. This double-layer capacitance includes in principle all electrostatic interactions of the ions (sulfate ions, etc.) and solvent molecules with the sensor electrode.

If a potential is applied between the sensor electrode 4 and the reference electrode 18 in order to enrich the substance, then the substance can be converted to an adsorbate such as

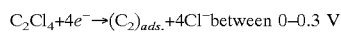
$$C_2Cl_4 + 4e^- \rightarrow (C_2)_{ads.} + 4Cl^- \text{ between } 0\text{–}0.3 \text{ V}$$

This adsorbate can consist of ions as well as neutral molecules with and without dipole character and forms an additional adsorbate layer on the particular electrode surface. This adsorbate layer blocks the sensor electrode 4 where it is adsorbed. Then at those places, the double-layer capacitance is reduced significantly because the distance of the double layer from the electrode surface is enlarged as a result of the adsorbate located in between.

In addition to the conversion of the substance to be detected to the adsorbate, in case of enrichment of the substance, at the same time, a competing electrochemical reaction can also occur, such as

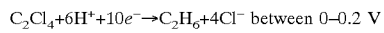
$$C_2Cl_4 + 6H^+ + 10e^- \rightarrow C_2H_6 + 4Cl^- \text{ between } 0\text{–}0.2 \text{ V}$$

Even at an optimum adsorption potential, possibly to a small extent, an undesirable competing electrochemical reaction of the substance to be detected can occur to a product which is no longer adsorbed. Furthermore, at potentials for the adsorption of the substance to be enriched, the oxygen of the air is also reduced, which leads to a large additional current which is highly superimposed onto the actual measured signal. These electrochemical reactions that occur parallel to the adsorption, are described with the aid of resistors 40a and 40b.

In addition to the double layer capacitance, another pseudocapacitance 34a and 34b also arises at the particular electrodes 4 and 14, due to the following effect: protons from the solution adsorb as hydrogen on the electrocatalyst 8—and the following reaction occurs on a platinum layer:

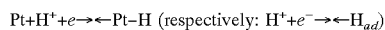
$$Pt + H^+ + e^- \rightleftharpoons Pt\text{-}H \text{ (respectively: } H^+ + e^- \rightleftharpoons H_{ad})$$

The current flowing as a result of this behaves exactly as a capacitive current, and, therefore, we speak of a pseudocapacitance 34a or 34b. This pseudocapacitance 34a or 34b is highly potential-dependent and is an order of magnitude larger than the actual double layer capacitance 32a or 32b. At the point of the sensor electrode 4, where the substance to be detected is adsorbed (irreversibly), no hydrogen can adsorb any longer, as a result of which, in addition to the double layer capacitance (see above), the pseudocapacitance 34a or 34b is also reduced.

Resistors 36a and 36b describe the limited rate of hydrogen adsorption. However, this rate is extremely high and the resistors 36a and 36b are thus correspondingly small, so that the double layer capacitances 32a and 32b as well as the pseudocapacitances 34a and 34b can hardly be distinguished from one another.

Instead of hydrogen adsorption, the adsorption of metal ions, such as copper, can also be utilized according to $$Cu^{2+} + 2e^- \leftrightarrows Cu_{ads}.$$

Since some of the substances to be detected prevent the adsorption of copper, in this way, the selectivity of sensor 2 can be increased. In this case, the value of the resistors 36a and 36b must be taken into consideration.

The reference electrode 18 is described by a complex impedance 18a. However, this impedance 18a, similarly to the current flowing through it, is so low that no potential drop occurs.

The ohmic resistance of the electrolyte solution before the particular electrode 4 and 14 is represented by an electrolyte resistor 38a and 38b. The ohmic resistance of the particular electrocatalyst layer is represented by the corresponding resistors 42a and 42b. However, it cannot be distinguished from the ohmic resistance of the electrolyte solution by technical measurements.

With the aid of the equivalent circuit shown in FIG. 2, the double layer capacitance (optionally also the pseudocapacitance) are derived from the measured impedance of the sensor electrode 4 through the imaginary part of the alternating current and correlated with the enrichment or with the time change of the enrichment. Then, from the time-dependent amount of enrichment, the concentration and the type of enriched substance can be determined.

Figure 3A:
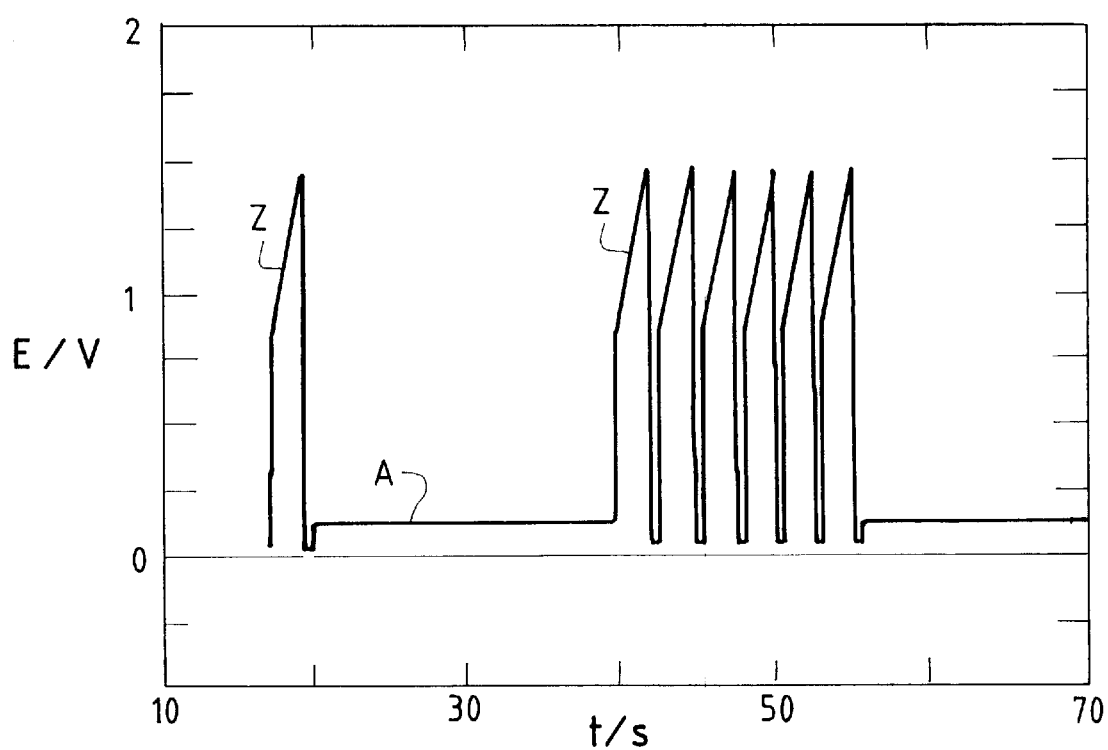
FIG. 3a is a diagram of a potential-time curve for the modified alternating-current method.
Figure 3B:
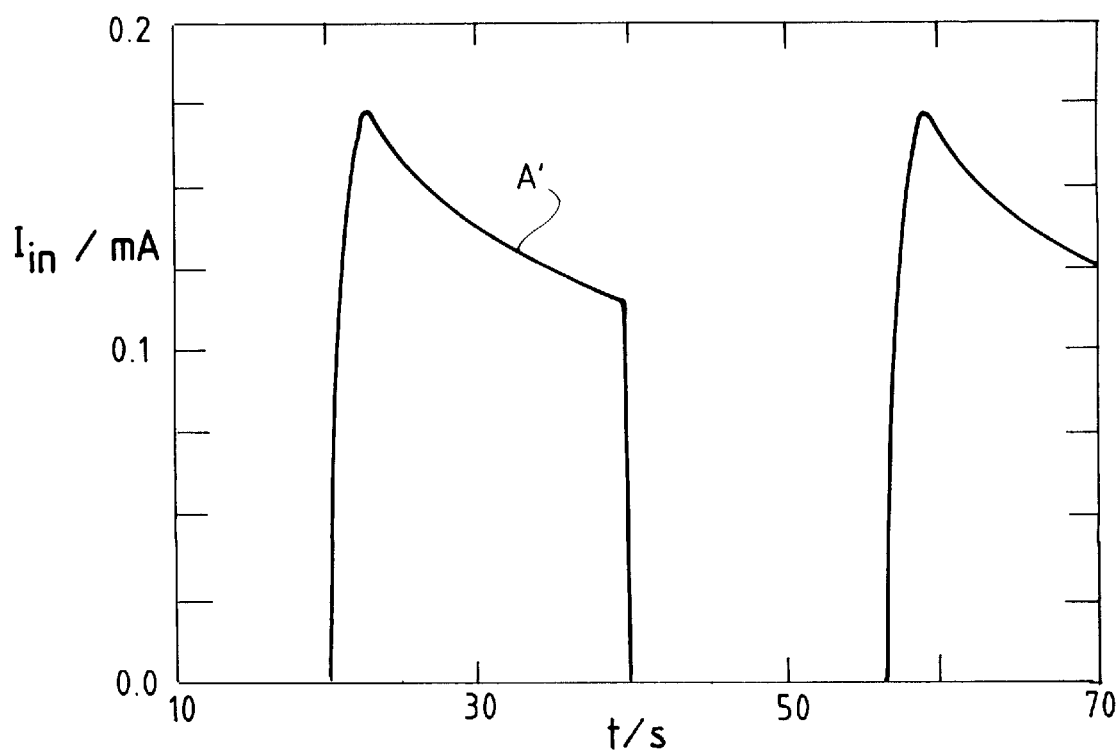
FIG. 3b is a diagram of the corresponding time curve of the imaginary part of the alternating current.

FIG. 3a shows a diagram of a potential-time curve for the modified alternating current method using the detection of perchloroethylene in synthetic air as example. FIG. 3b shows a corresponding time plot of the alternating current imaginary part called alternating current transient A' below. In FIGS. 3a and b, the ordinate gives the potential in volts and the imaginary part of the alternating current in milliamperes and the abscissa shows the time in seconds. The electrode surface is a platinum layer in this example and the electrolyte solution contains 1 M $HClO_4$ as supporting electrolyte.

In the first detection step Z (FIG. 3a)—also called desorption Z below—the electrode surface is freed from any impurities present using an oxidation-reduction reaction and is activated. For this purpose, the potential applied to the sensor electrode 4 is increased or decreased to values at which any substances adhering to the electrode surface are reacted electrochemically and desorbed.

In a second detection step A—also called enrichment A below—a dc potential is applied at which, when possible, no electrochemical reaction of the substance to be detected is catalyzed in the neighborhood of the electrode, but rather, as selectively as possible, the substance to be detected is enriched. The accurate value for this potential depends on the thermodynamic and kinetic properties of the substance to be enriched. The enrichment rate is also dependent on the applied potential. For example, perchloroethylene becomes enriched as a potential value of 100 mV with a high rate of enrichment.

In the modified alternating current method, during enrichment A, an alternating voltage with an amplitude of 10 mV and a frequency of 10 Hz is superimposed onto the dc potential. The alternating current flowing A' (FIG. 3b) is recorded by the sensor electronics as a measured signal. For the evaluation of the measured signal, the initial drop of the alternating current transient A' is taken, is related to the enrichment rate and this is correlated with the concentration of the enriched substance. As can be seen in FIGS. 3a and b, the beginning of enrichment A and the use of a constant alternating current transient A' are shifted in time with respect to one another, which is caused by the process of establishment of the enrichment potential, by the electrolyte resistance or also by the measurement technology. This modified alternating current method is characterized by high linearity within the measured signal and substance concentration, because the enrichment rate can be measured almost directly and can be represented as a simple function of the concentration.

After the enrichment A, desorption steps Z are performed in order to desorb the enriched substance as completely as possible from the electrode surface via an oxidation or reduction reaction. After the fifth desorption step Z, consequently, the sensor electrode is sufficiently purified and, at the same time, activated again.

The amount of enriched substance contributes significantly to the sensitivity of sensor 2. In order to ensure that sensor 2 is equally sensitive, even at different substance concentrations, the alternating current transient A' is followed during the entire enrichment A and whether or not a sufficient amount of substance has been enriched is derived from this.

Figure 4A:
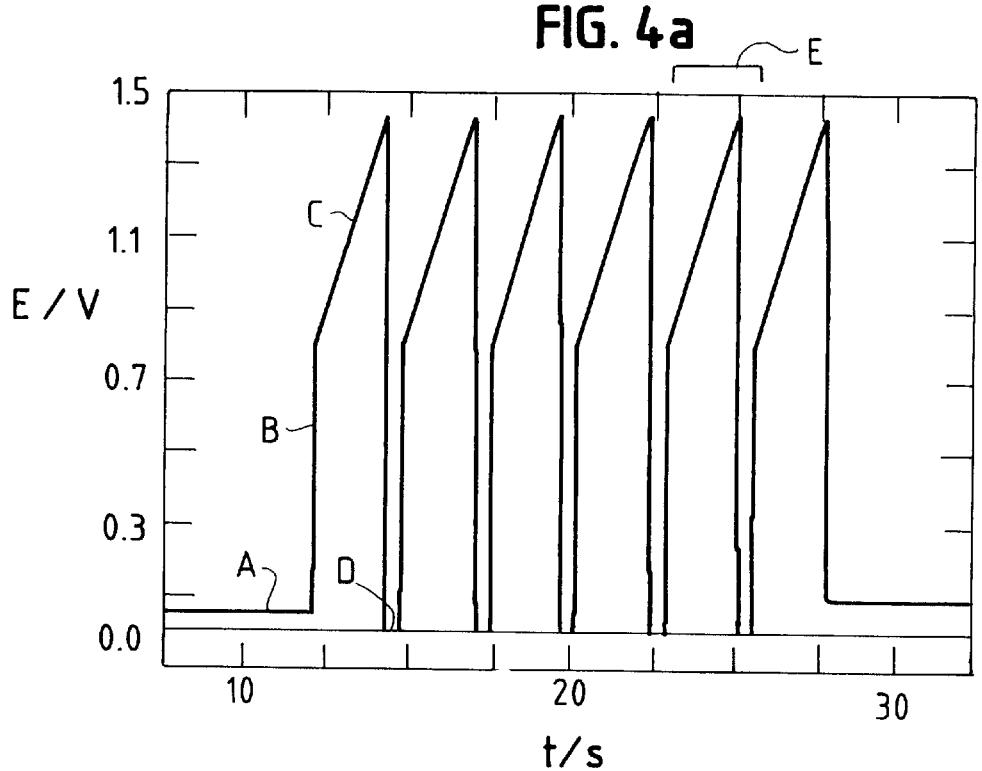
FIG. 4a is a diagram of a potential-time curve for the liquid phase potential method for the qualitative and quantitative detection of a substance.

FIG. 4a shows a diagram of a potential-time curve for one of the potential methods for the selective quantitative detection of the substance to be detected. In the diagram, the ordinate gives the potential in volts and the abscissa shows the time in seconds. The potential-time curve is shown for the example of a detection of benzene in the liquid phase (as well as in the gaseous phase) on a sensor electrode 4 sputtered with platinum.

In a first detection step, the enrichment step A, a potential of 200 to 300 mV is applied at sensor electrode 4 for 20 seconds in order to enrich a certain amount of the substance to be detected. As it is known from heterogeneous catalysis, here the internal bonds of the enriched or adsorbed substance are weakened. A subsequent oxidation can then occur at lower potentials than that needed for the oxidation of a free, that is, not adsorbed substance. During the enrichment or adsorption of the substance, oxygen of the air is reduced simultaneously. This leads to a large negative current (not shown) at sensor electrode 4, but this has no influence on the detection process.

In a second detection step B—also called potential jump B below—the potential is changed suddenly to 900 mV. This potential value is chosen so that oxidation of the enriched substance or layer just does not occur.

In a third detection step C—also called oxidation C below—the potential is increased linearly in time with a potential change rate of 300 mV/s. Hereby, the enriched layer becomes oxidized and at the same time, largely desorbed—for example, benzene becomes oxidized at platinum electrodes according to $$(C_6H_6)_{ads.} + 12H_2O \rightarrow 6CO_2 + 30e^- + 30H^+.$$

At potentials higher than about 0.7 V, additionally, the oxygen bound in the electrolyte liquid begins to adsorb:

$$H_2O \rightarrow O_{ads.} + 2e^+ 2H^+.$$

Here, a clearly defined oxide layer is formed as a monolayer. In some cases, the already adsorbed substance to be detected (benzene) and now to be reacted electrochemically, is to be displaced at sensor electrode 4:

$$(C_6H_6)_{ads.} + H_2O \rightarrow C_6H_6 + O_{ads.} + 2H^+ + 2e^-.$$

The potential steps serve to achieve oxidation and desorption of the enriched substance as completely as possible.

In a fourth detection step D—also called reduction D below—the potential is reduced again to a highly cathodic potential of 50 mV for a fraction of a second (for example, 0.5 sec); this potential corresponds approximately to the enrichment potential. The time for the fourth detection step D is chosen to be so short that the substance to be detected cannot be deposited on the electrode surface again and, on the other hand, the entire oxide layer will be reduced and desorbed.

The three detection steps, B, C and D, that is, the potential jump B, oxidation C and reduction D form a detection cycle E. This detection cycle E is repeated five times in succession. As a result of this, the substance to be detected and additionally enriched substances are removed completely from the electrode surface until finally only the clearly defined oxide covering layer that is formed again in the detection cycle E remains. It can be assumed that no enriched substance is present on the electrode surface any longer in the fifth detection cycle E.

Figure 4B:
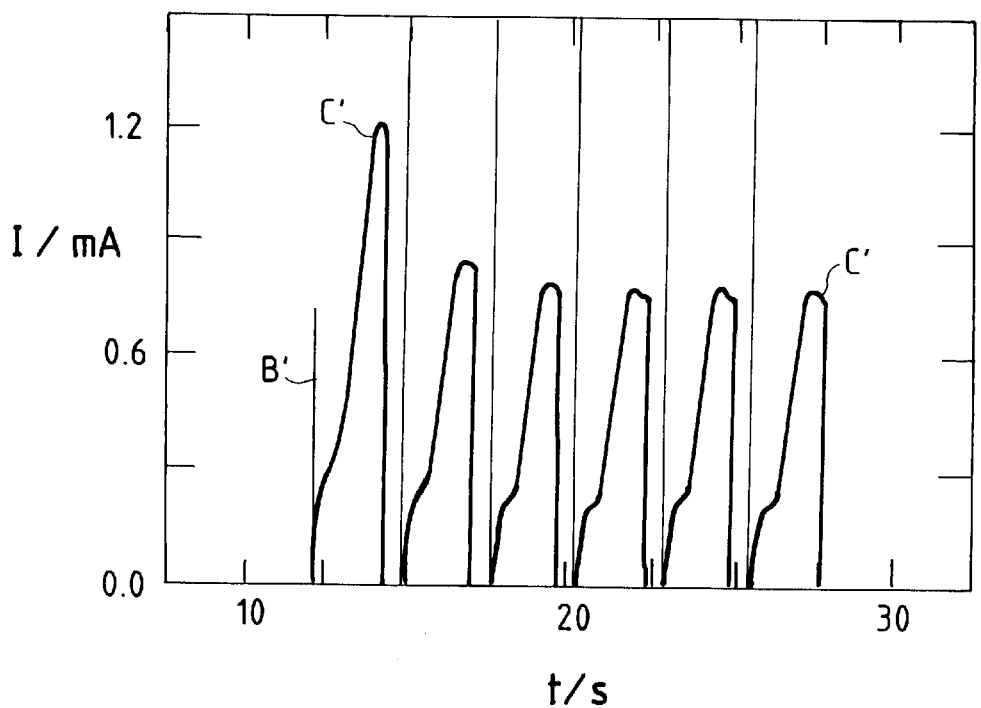
FIG. 4b is a diagram of a corresponding current-time curve.

FIG. 4b shows a diagram of the current-time curve, which flows as a result of the potential program shown in FIG. 4a. In the diagram, the ordinate gives the current in milliamperes and the abscissa gives the time in seconds.

The current-time curve shows a current peak B' and a subsequent oxidation current C' for each detection cycle E of the potential-time curve.

The current peak B' occurs during the potential jump B and results from the recharging of the produced double layer at the sensor electrode 4.

The oxidation current C' increases strongly to a maximum, which is at the highest potential value of the potential range of oxidation C in the practical example shown in FIG. 4b. This maximum can also be reached at a different value of the potential of the potential range. The oxidation current C' results from a superimposition of two currents, one of which flows because of the oxidation C of the substances to be detected, enriched and additionally enriched and the other flows because of the development of the oxide layer on the electrode surface. The maximum of the oxidation current C' decreases steadily from the first to the fifth detection cycle E. In the fifth detection cycle E, the magnitude of the current that flows due to the oxidation C of the enriched substances is so small that only the development of the oxide layer contributes to the oxidation current C'. For example, in the example of benzene, the oxidation current C' is measured at 1.44 V.

A measured signal to be correlated to the concentration is obtained, for example, by forming the difference between the measured oxidation currents C' in the first and in the fifth detection cycles E. The potential at which these two oxidation currents C' are measured within a detection cycle E can be chosen in such a way that the resulting difference is maximum. In this example, the difference of the maximum values of the oxidation currents C' is formed.

The enrichment of a substance at the electrode surface is influenced significantly by the properties of this surface. Thus, the obtained measured signal should be suitably normalized in order to be able to be reproduced well. For this normalization, the difference of the oxidation currents C' in the first and in the fifth detection cycles E is formed and normalized to the oxidation current C' determined in the fifth detection cycle E. The oxidation current C' measured in the fifth detection cycle E reflects the real surface conditions that influence the enrichment conditions. After this normalization, the measured signal is a dimensionless quantity.

The sensitivity of sensor 2 is greatly improved by enrichment A. The oxidation current C', which flows during the electrochemical reaction of the enriched substance, which is to be correlated with the concentration, is dependent on the amount of substance accumulated during the enrichment A. Thus, the measured signal is influenced considerably by the amount of time available for the enrichment A. This time can also be optimized automatically by measuring the electrode capacitance. For this purpose, the enrichment potential is applied only until the electrode capacitance reaches a predetermined value. For the detection of benzene, concentrations to 1 ppm can be detected reliably. (For example, perchloroethylene can be detected to 30 ppm, but with an improved evaluation electronics even to 3 ppm.)

The duration of a detection with 5 detection cycles E takes, for example, 20 seconds for benzene (for example, 36 seconds for perchloroethylene).

On the other hand, the selectivity of the sensor 2 is dependent on the selection of the electrode material and of the electrolyte. Moreover, the maximum potential-dependent enrichment rate and also the potentialdependent oxidation current C flowing during the electrochemical reaction play a significant role, since different substances are oxidized or, in the reverse case, reduced, at different potentials. In the method presented here, several measurement parameters are available for increasing the selectivity of the measured signal. On the side of the sensor, this includes the electrode material and the electrode metal, the electrolyte, the pH value of the electrolyte solution and the material of the film on the solution side (in the case of a sensor for the liquid phase). The extent and the rate of adsorption of the substance to be detected can be influenced by ions or additives in the electrolyte, which themselves adsorb at a certain potential without being reacted. This effect depends strongly on the nature of the substance to be detected and therefore leads to a higher selectivity of the sensor. On the electronics side of the sensor, these measurement parameters include the adsorption potential, the oxidation potential (in the case of linear potential ranges, this corresponds to the potential at which the oxidation current is detected), the time at which—in the case of oxidation at constant potential—the oxidation current is detected, and the slope of the potential range (different substances are oxidized at different rates). The special advantage of the electronically alterable parameters lies in the fact that they can be altered automatically or manually very rapidly.

Figure 5:
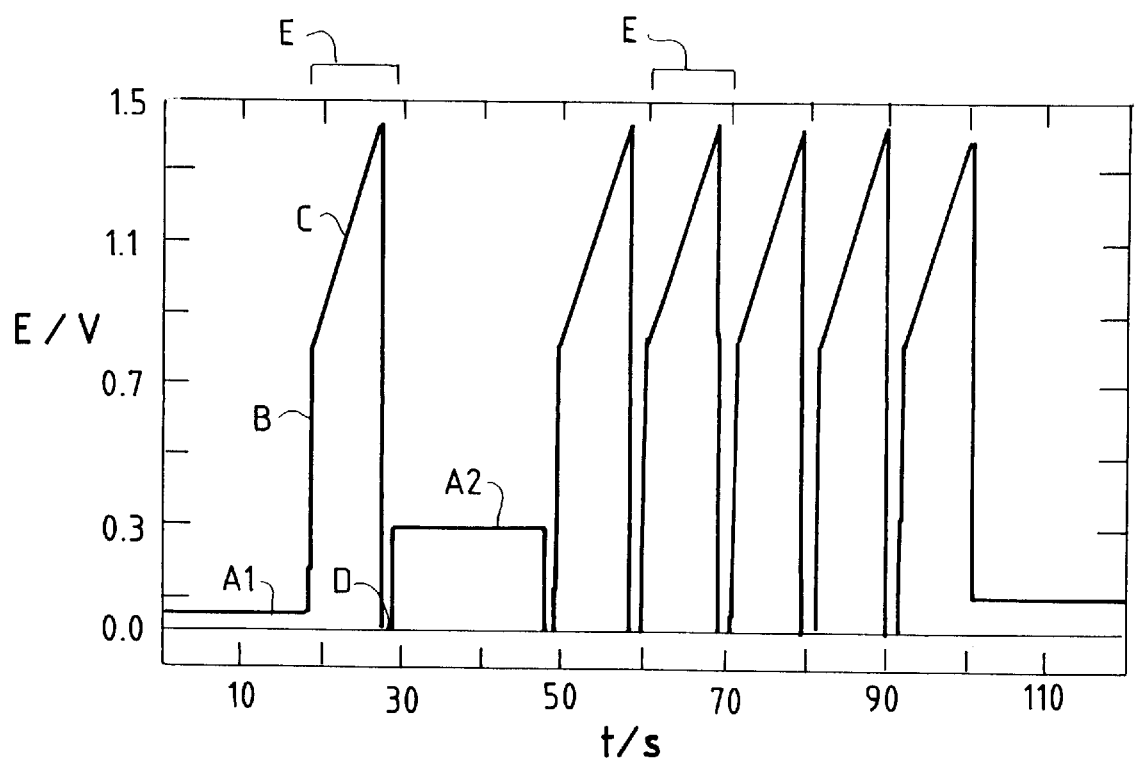
FIG. 5 is a diagram of a potential-time curve for the general potential method for the qualitative and quantitative detection of two substances.

FIG. 5 shows a diagram of a potential-time curve for the general potential method for the detection of two substances. In the diagram, the ordinate shows the potential in volts and the abscissa the time in seconds. The detection of two substances to be detected will be explained on the example of perchloroethylene and toluene in air using a platinum-coated electrode surface and a 1M $HClO_4$ electrolyte solution.

In a first detection step A1, a low potential of 50 mV is applied to the sensor electrode 4 for 20 seconds, during which both the perchloroethylene as well as the toluene become enriched at the electrode surface.

In a second detection step B—also called potential jump B below—the potential is increased suddenly to 900 mV.

The magnitude of this potential value is chosen so that oxidation of the two enriched substances still does not occur.

In a third detection step C—also called oxidation C below—the potential is increased linearly in time at a potential increase rate of 300 mV/s. During this, the two enriched substances are oxidized.

In a fourth detection step D—also called reduction D below—the potential is decreased suddenly to a low potential at which the adsorbed oxygen is reduced and any residues of toluene and perchloroethylene present are desorbed.

The three detection steps B, C and D again form a detection cycle E. This detection cycle E can be repeated five times in succession (not shown). As a result of this, the toluene and perchloroethylene are removed from the electrode surface as completely as possible.

In a fifth detection step A2, a low potential of 300 mV is applied to the sensor electrode 4 at which mainly only toluene is enriched. Then the potential jump B, oxidation C and reduction D are repeated, where, during oxidation C, only the enriched toluene is oxidized. Perchloroethylene would also become oxidized at the applied potential. However, due to the exclusive enrichment of toluene in the fifth detection step A2, this oxidation of perchloroethylene is eliminated.

Subsequent detection cycles E follow, consisting of potential jump B, oxidation C and reduction D in order to determine the oxygen adsorption on the electrode surface and the changes of the electrode surface. During the entire detection, the current-time curve is measured and recorded in order to correlate the corresponding current values with the substance concentrations. However, it is also sufficient to report only the current values during the oxidation at the maximum or at a characteristic is potential. For this purpose, first, the oxidation currents are measured that arise from the oxidation C of the first enriched layer—consisting of perchloroethylene and toluene—and from the oxidation C of the second enriched layer—consisting largely of toluene. Analogously to the detection method shown in FIGS. 4a and 4b, the difference values of the oxidation currents measured in the first and fifth detection cycles E are determined.

The difference value obtained in this way, which originates from the oxidation C of the second enriched layer—consisting largely of toluene—is a measure of the toluene concentration in the investigated substance mixture, since the portion of the current to be attributed to the adsorption of oxygen is eliminated from the oxidation current C'. The difference of the difference values obtained above is again a measure of the perchloroethylene concentration, since the part of the oxidation current C, attributable to oxygen adsorption as well as to oxidation of toluene is eliminated.

Thus, corresponding to the applied potential program, the sensor 2 can distinguish between different substances to be detected. This applies especially to substances to be detected in a mixture, where the enrichment potentials differ greatly—such as perchloroethylene and toluene, benzene or vinyl acetate. These can also be enriched at considerably more anodic potentials.

Figure 6A:
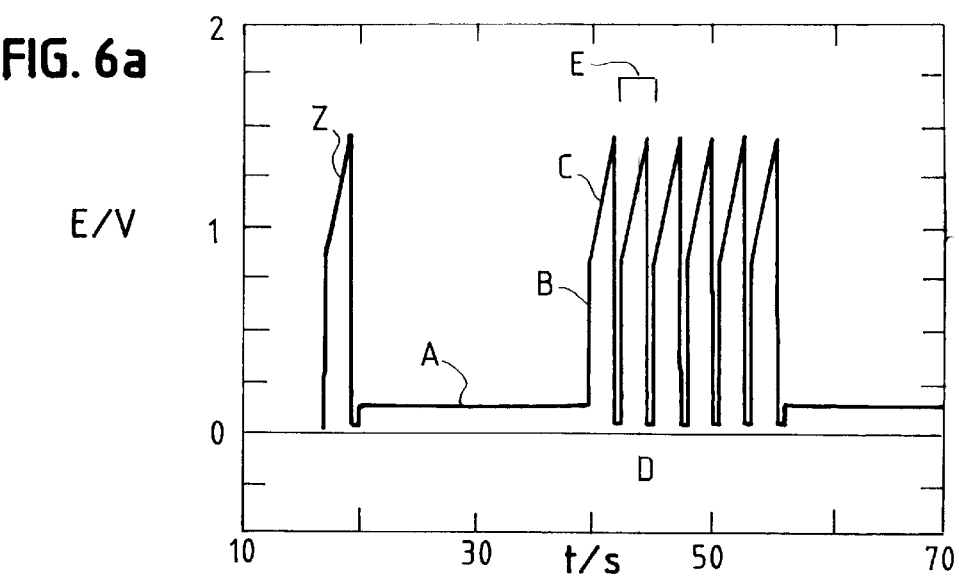
FIG. 6a is a diagram of a potential-time curve for the combined detection method.
Figure 6B:
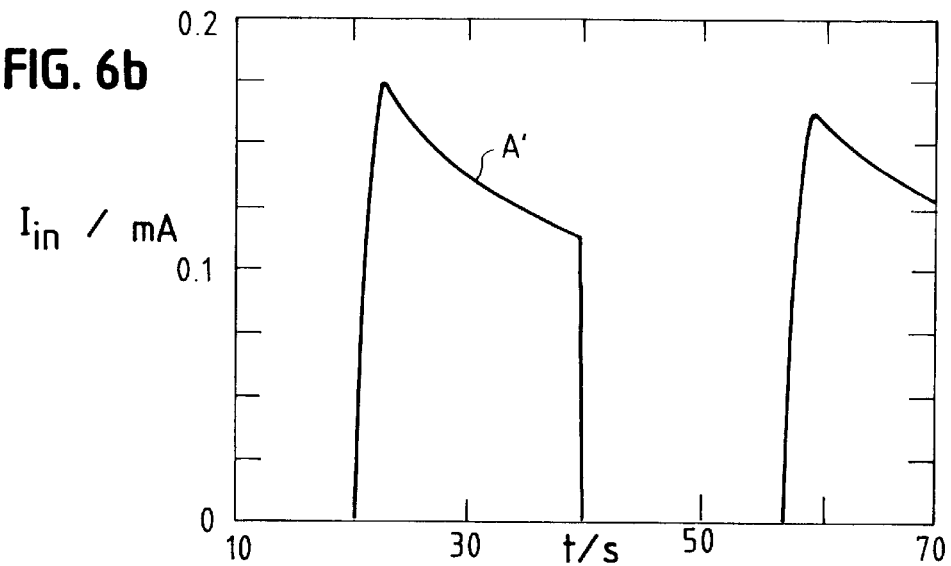
FIG. 6b is a diagram of a corresponding time curve of the imaginary part of the alternating current.
Figure 6C:
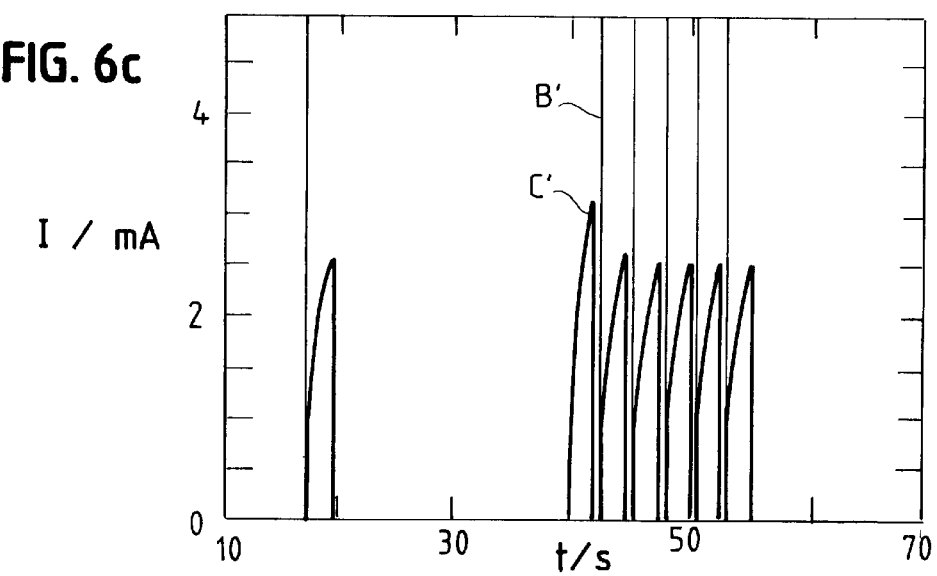
FIG. 6c is a diagram of a corresponding dc current—time curve.

FIGS. 6a–c show in diagrams a potential-time curve (FIG. 6a), a corresponding alternating current transient A' (FIG. 6b) and a corresponding dc time curve C' (FIG. 6c) for the combined detection method, that is, for the measurement of the electrode capacitance during substance enrichment and the measurement of the current during the subsequent electrochemical reaction of the substance(s) thus enriched. In the diagram of FIG. 6a, the ordinate gives the potential in volts and the abscissa the time in seconds. In the diagrams of 6b and 6c, the ordinate gives the imaginary part of the alternating current and the direct current in mA, respectively, the abscissas show the time in seconds.

A low frequency alternating voltage is superimposed on the established potential value during enrichment A. As in the modified alternating current method, thus, by measuring the alternating current transients, the enrichment of the substance to be detected on the electrode surface is followed. The electrochemical reaction or oxidation C is started only when a sufficient amount of substance has been enriched on the electrode surface. The resulting oxidation current C' thus yields a sufficiently large measured signal and thus a reliable determination of the concentration of the enriched substance. This concentration determination is related to the enrichment time in order to obtain the actual concentration of the substance to be detected in the investigated mixture.

Thus, in this method presented here, the enrichment time is no longer constant, but is adapted automatically to the existing substance concentration. A shorter enrichment time is sufficient for a higher substance concentration, while a lower substance concentration requires a longer enrichment time in order to enrich a sufficient amount of substance on the electrode surface. Furthermore, this method offers advantageously a continuous function control of the sensor by measuring the current in the fifth detection cycle and the capacitance without enrichment.

What is claimed is:

1. Method for continuously detecting at least one substance in a gaseous or liquid mixture with a sensor electrode having a capacitance, said method comprising the steps of:
    (a) enriching the substance on the surface of the sensor electrode by applying an adsorption potential characteristic for the substance to be detected;
    (b) determining the enrichment by measuring the electrode capacitance of the sensor electrode;
    (c) completing the enrichment when the electrode capacitance or the change of the electrode capacitance as a function of time reaches a predetermined value;
    (d) bringing the potential to a potential which is characteristic for the electrochemical reaction of the substance to produce a current;
    (e) measuring the current thus produced; and
    (f) correlating the measured current value thus obtained with at least one of the type and concentration of the substance.

2. Method according to claim 1, comprising the step of determining the concentration of the substance from the difference of the electrode capacitance of the sensor electrode, without and with enrichment of the substance on the electrode surface.

3. Method according to claim 1, comprising the step of determining the concentration of the substance from the time change of the electrode capacitance of the sensor electrode.

4. Method according to claim 1, comprising the steps of first electrochemically reacting the substance to be detected at the sensor electrode or at another electrode at an applied potential and then detecting at least one product thus obtained with the sensor electrode.

5. Method according to claim 1, comprising the step of optimizing the detection by varying a parameter selected from the group consisting of electrode material, electrolyte composition, enrichment, enrichment potential, potential for electrochemical reaction, and change of the potential for electrochemical reaction as a function of time.

6. Method according to claim 1, comprising the step of changing the potential characteristic for the electrochemical reaction linearly as a function of time.

7. Method according to claim 1, comprising the step of determining the concentration of the substance at a given potential through the current produced during the electrochemical reaction.

8. Device for continuously detecting at least one substance in a gaseous or liquid mixture, comprising:

(a) a sensor electrode having a capacitance;

(b) means for applying at the sensor electrode a potential characteristic for the enrichment of the substance at the surface of the sensor electrode;

(c) means for measuring the electrode capacitance of the sensor electrode as a result of the enrichment;

(d) means responsive to the measuring means for automatically completing the enrichment when the electrode capacitance or the change of electrode capacitance as a function of time has reached a predetermined value;

(e) means for bringing the potential to a potential which is characteristic for the electrochemical reaction of the substance to produce a current;

(f) means for measuring the current thus produced; and (g) means for correlating the measured current value thus obtained with at least one of the type and concentration of the substance.

9. Device according to claim 8, comprising:

(h) a sensor comprising an electrolyte a membrane separating the electrolyte from the mixture, and a sensor electrode neighboring the membrane; and (i) means for introducing the mixture to the side of the membrane opposite the electrolyte.

10. Device according to claim comprising a noble metal layer on one side of the membrane.

* * * * *